United States Patent
Masoud et al.

(10) Patent No.: US 7,742,822 B2
(45) Date of Patent: Jun. 22, 2010

(54) CHANNEL SELECTION AND MAPPING FOR MEDICAL DEVICE COMMUNICATION

(75) Inventors: Javaid Masoud, Shoreview, MN (US); Charles H. Dudding, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 507 days.

(21) Appl. No.: 11/739,295

(22) Filed: Apr. 24, 2007

(65) Prior Publication Data

US 2008/0264431 A1    Oct. 30, 2008

(51) Int. Cl.
   *G08C 17/00* (2006.01)
(52) U.S. Cl. .................. 607/60; 607/32; 340/539.12
(58) Field of Classification Search ............... 607/32, 607/60
   See application file for complete search history.

(56) References Cited

U.S. PATENT DOCUMENTS

| | | |
|---|---|---|
| 5,822,681 A | 10/1998 | Chang et al. |
| 6,389,284 B1 | 5/2002 | Cook et al. |
| 6,535,766 B1 | 3/2003 | Thompson et al. |
| 6,801,807 B2 | 10/2004 | Abrahamson |
| 6,807,163 B1 | 10/2004 | Shi |
| 7,280,872 B1 * | 10/2007 | Mosesov et al. ............ 607/60 |
| 2005/0137480 A1 | 6/2005 | Alt et al. |
| 2006/0148482 A1 | 7/2006 | Mangold |

* cited by examiner

*Primary Examiner*—Carl H Layno
*Assistant Examiner*—Yun Haeng Lee
(74) *Attorney, Agent, or Firm*—Stephen W. Bauer; Michael J. Ostrom

(57) ABSTRACT

Embodiments of the invention include channel selection and mapping for medical device communication. The communication system can implement a two-stage listen before talk protocol to choose a channel for communication. The first stage samples the interference of each channel for a relatively short time and chooses the best signal. The second stage samples the channel selected by the first stage and samples it for a relatively longer time to confirm the channel selected by the first stage is the best channel for communication.

19 Claims, 3 Drawing Sheets

CHANNEL SELECTION AND MAPPING FOR MEDICAL DEVICE COMMUNICATION

FIELD

The disclosure relates to medical device communication.

BACKGROUND

Medical devices often communicate with each other and with various other devices via radio frequency (RF) communication. Unfortunately, as the number of communicating devices has grown, the bandwidth relegated to handle these types of communications has become busy. This can lead to interference with the communication by other devices attempting to communicate on the same frequency.

DETAILED DESCRIPTION OF THE ILLUSTRATED EMBODIMENTS

Figure 1:
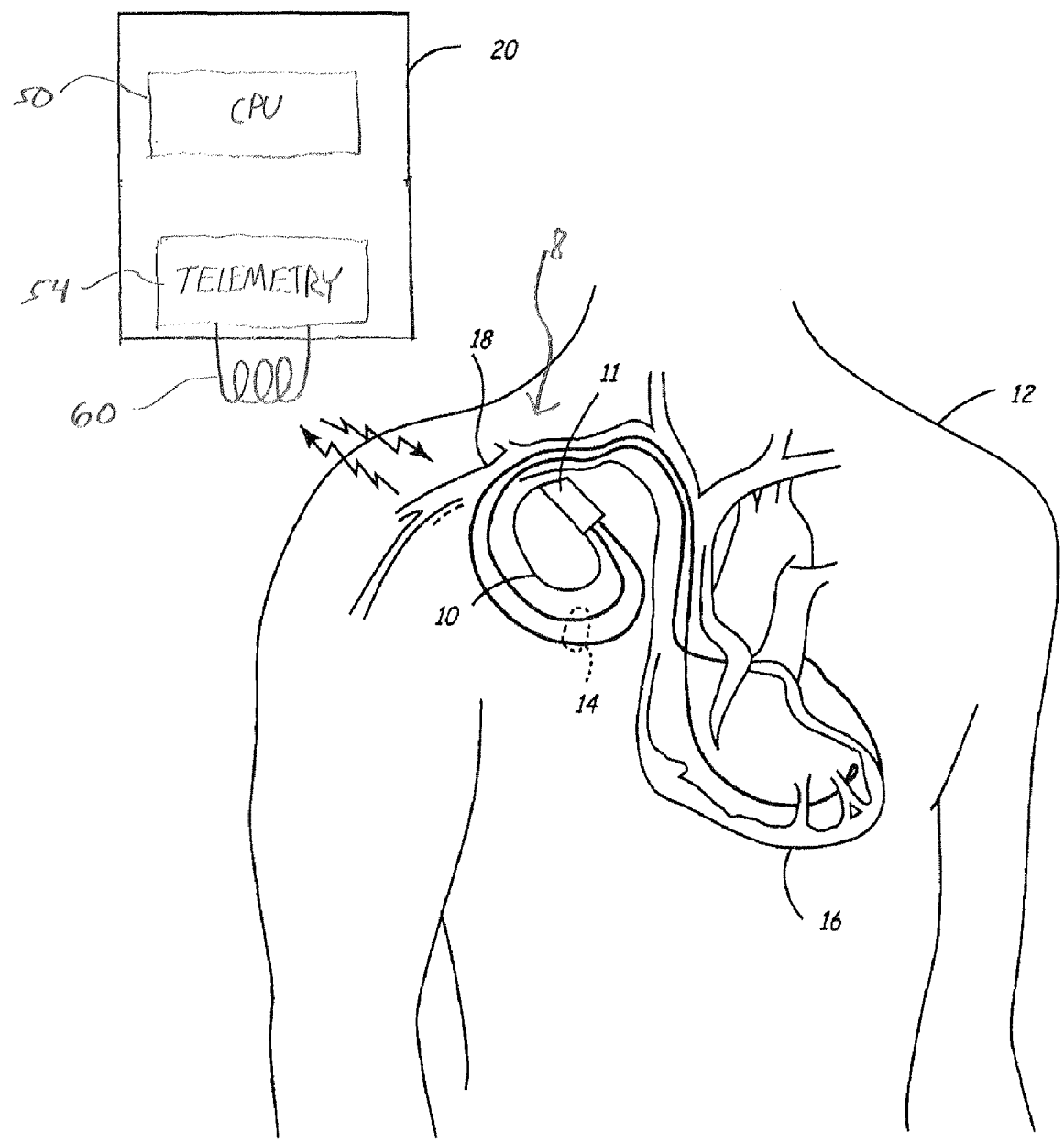
FIG. 1 is a diagram depicting a first device and a second device communicating via RF communication.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Radio frequency (RF) technology permits wireless communication between physically separated devices, which for convenience will be referred to as first and second devices. First and second devices may each independently include, for example, a medical device and/or a supporting device, such as a programmer and/or monitoring system. A medical device may include, or may be adapted for use in, for example, implantable medical devices (IMDs) with or without transvenous leads, including implantable hemodynamic monitors (IHMs), implantable cardioverter-defibrillators (ICDs), cardiac pacemakers, cardiac resynchronization therapy (CRT) pacing devices, implantable subcutaneous monitoring devices, implantable subcutaneous therapy devices (e.g., such as defibrillation devices), drug delivery devices, or combinations of such devices. Some embodiments of the invention may also include, or may be adapted for use in, medical devices which are not generally implantable, such as, for example, patient companions, glucose monitors, external sensors, or combinations of such devices.

Some embodiments of the invention include a system and method of wireless communication (e.g., radio frequency (RF) communication) between a first device and a second device, wherein at least one of the first device and second device is a medical device. Before communicating, either the first device or the second device initiates a listen before talk (LBT) protocol to avoid communicating on a busy channel. The LBT protocol includes a stage one analysis wherein more than one channel is sampled for interference for a first interval (i.e., a first stage interval) and the best channel is selected. Next, a stage two analysis is conducted wherein the channel chosen by the stage one analysis is sampled for interference for a second interval (i.e., a second stage interval). The second interval can be longer than the first interval. The stage two analysis allows the communicating device to efficiently determine if the channel selected by the stage one analysis is the best channel for communication because the longer sampling time of the stage two analysis will discover pulsed and intermittent communications that may not have been identified in the relatively short sampling time of the stage one analysis.

A representative example of a first device 8 useful in some embodiments of the invention includes a pacemaker, which will now be described in further detail. An embodiment of pacemaker 10 implanted in a patient 12 is shown in FIG. 1. As shown, pacemaker 10 is housed within a hermetically sealed, biologically inert outer canister or housing. One or more pacemaker leads, collectively identified with reference numeral 14 in FIG. 1, are electrically coupled to pacemaker 10 and extend into the patient's heart 16 via a vein 18. Disposed generally near the distal end of leads 14 are one or more exposed conductive electrodes for receiving electrical cardiac signals or delivering electrical pacing stimuli to the heart 16.

Figure 2:
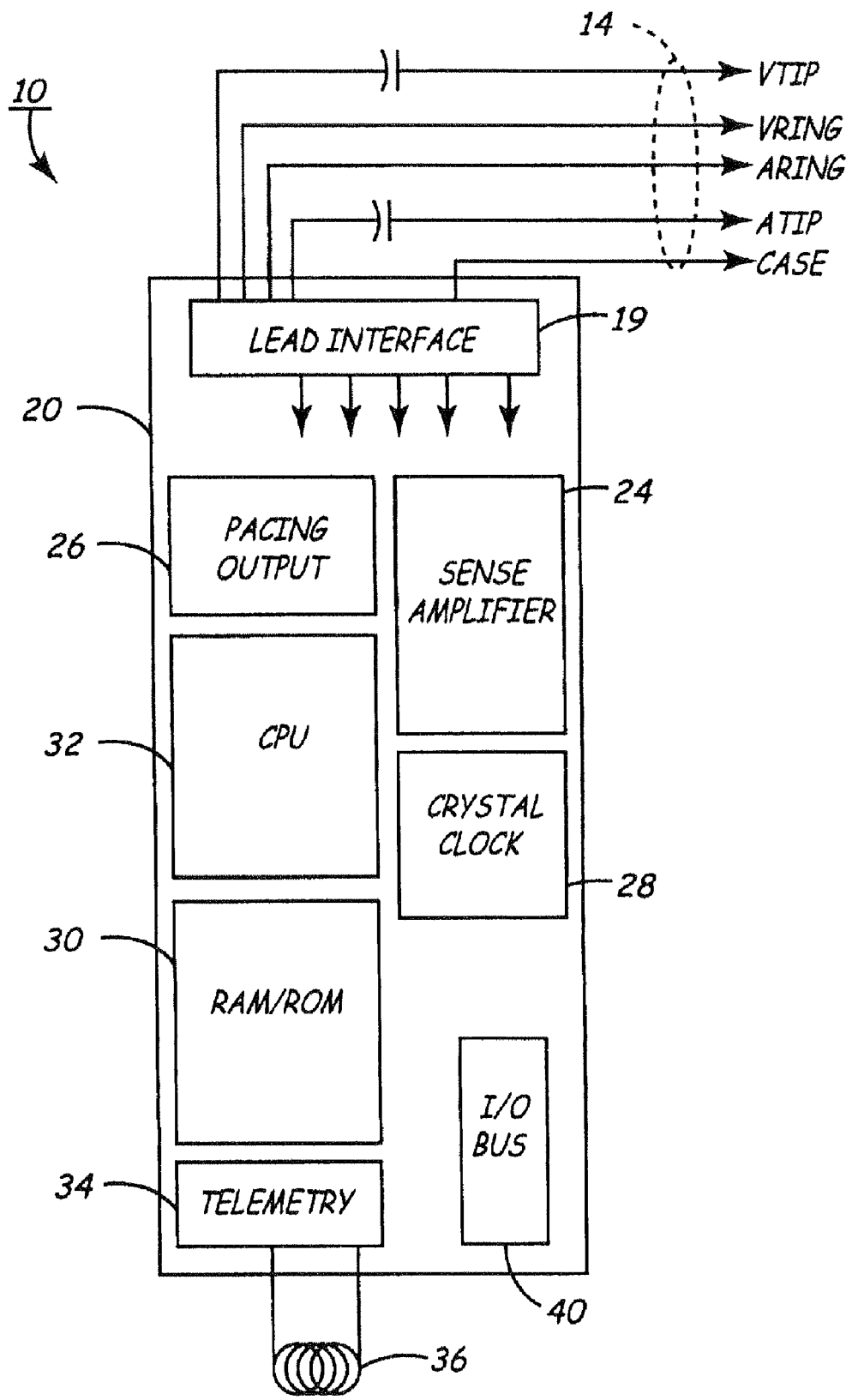
FIG. 2 illustrates a medical device circuitry in accordance with an embodiment of the invention.

FIG. 2 provides a block diagram of an embodiment of electronic circuitry that makes up pacemaker 10 for delivery of electrical stimulation therapy to the patient. FIG. 2 shows that pacemaker 10 comprises circuitry for controlling the device's pacing and sensing functions. Pacemaker 10 can also include various other components, such as a sense amplifier circuitry 24, a stimulating pulse output circuitry 26, a crystal clock 28, a random-access memory and read-only memory (RAM/ROM) unit 30, and a pacing timing and control circuit in the form of a programmed central processing unit (CPU) 32. Pacemaker 10 can also include an internal telemetry communication circuit 34 coupled to antenna 36 so that it is capable of RF communication with a second device 20, such as an external programmer/control unit. Further, pacemaker 10 can be powered by a battery (not shown).

With continued reference to FIG. 2, pacemaker 10 is coupled to one or more leads 14 which, when implanted, extend transvenously between the implant site of pacemaker 10 and the patient's heart 16, as previously noted with reference to FIG. 1. Physically, the connections between leads 14 and the various internal components of pacemaker 10 are facilitated by a conventional connector block assembly 11, as shown in FIG. 1. Electrically, the coupling of the conductors of leads and internal electrical components of pacemaker 10 may be facilitated by a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components. For the sake of clarity, the specific connections between leads 14 and the various components of pacemaker 10 are not shown in FIG. 2, although it will be clear to those of ordinary skill in the art that, for example, leads 14 will be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14.

As stated above, first device may wirelessly communicate with a second device, which may include another medical device and/or a programmer or monitoring system. FIG. 1 also depicts a second device 20 (e.g., an external programming unit) for RF communication with medical device 10. Second device 20 may communicate with medical device 10 via one or more antennas that can send RF signals to, and receive RF signals from, an antenna associated with the medical device. In embodiments where the first device 8 is an implantable medical device, second device 20 provides a non-invasive means for communicating with the medical device. Second device 20 can be equipped with circuitry that allows it to wirelessly communicate with first device 8, such as a central processing unit (CPU) 50 and an internal telemetry communication circuit 54 coupled to an antenna 60, as shown in FIG. 1.

In some embodiments, first and second devices may communicate in a range of about two to about five meters, such as in a typical operating suite or follow-up environment. Longer distances may be achieved depending on local conditions such as other transmitters, sources of noise, or the physical attributes of the communication space.

Radio frequency communications between the first and second devices may take place within any available frequency band. Federal Communications Commission Regulations found in 47 C.F.R. include provisions that concern medical device implant communications in the 402-405 MHz frequency band. These provisions include what is referred to as the "Medical Implant Communications Service" (MICS) and address certain performance characteristics of a communications channel to be used for RF communications with a medical device. In Europe, similar standards are set forth by the European Telecommunication Standard Institute (ETSI). ETSI's standard document EN 301 489-27 covers radio equipment in the frequency range 402 MHz to 405 MHz for Ultra Low Power Active Medical Implants and Accessories. Further, the "Medical Data Service" (MEDS) concerns medial device communication in the 401-402 MHz and 405-406 MHz frequency bands. In some embodiments, RF communications between the first and second devices take place within the MICS and/or MEDS band.

Figure 3:
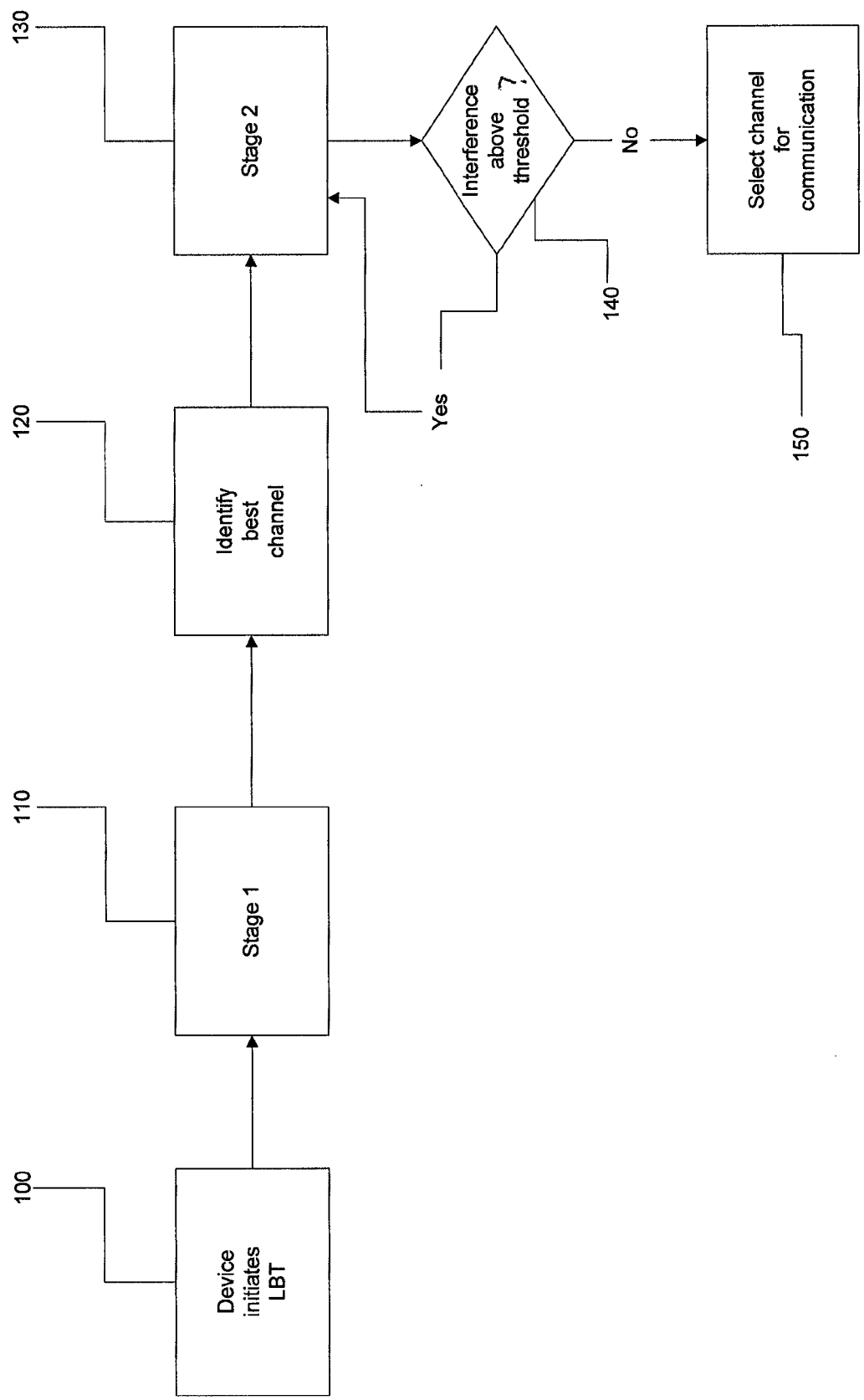
FIG. 3 is a flow chart depicting a method in accordance with an embodiment of the invention.

In some embodiments the first and second devices may selectively communicate on several (e.g., 10) channels within the MICS and/or MEDS band. Further, some embodiments of the invention include a system and method for selecting the relatively least interfered-with channel for communication. FIG. 3 shows a flow chart depicting a method in accordance with an embodiment of the invention. In the first step of this embodiment, either the first or second device initiates a LBT protocol at block 100 to determine the level of activity within the MICS and/or MEDS band before communicating. A LBT protocol allows the device wishing to establish a communication link to first monitor channels in the band for potentially interfering activity during a set interval before communicating.

In some embodiments, LBT protocol includes a first stage analysis, as depicted by block 110, wherein the device monitors each channel for a set interval before selecting the channel. For example, the set interval can be from about 1 milliseconds (msec) to about 10 msec (e.g., about 10 msec). During the first stage analysis, relative values of interference based on, for example, peak amplitude can be assigned to each channel and stored for later calculations, and the best channel can be identified as shown in block 120.

Many medical devices intermittently transmit data in pulsed signals. Some medical devices duty cycle their use of the communications channel in order to preserve battery power. In some instances, a device's duty cycle is configured so that it may not communicate frequently enough, or for a long enough period, to be detected by a device implementing the relatively short sampling time of the first stage analysis. For example, a device may cease communicating for periods longer than 10 msec. Further, initially sampling each channel for a long sampling time will in many cases waste time because it is believed that one of the top few channels identified by the stage one analysis will ultimately prove to be the least interfered with channel.

Continuing with reference to FIG. 3, some embodiments of the LBT protocol include a second stage analysis, as shown in block 130, to be performed after identifying the best channel as determined by the first stage analysis. In some embodiments, the second stage analysis includes sampling the best channel selected by the first stage analysis for a longer sampling time than was performed in the first stage analysis. For example, the best channel may be sampled between about 10 msec and about 100 msec (e.g., about 50 msec). This further analysis allows the device to detect channel activity that is present although the first stage analysis did not detect the activity.

In some embodiments, the stage two analysis first samples the channel with the lowest level of detected activity (the "best" channel), as determined in the first stage analysis. The next best channel's relative interference value, as determined by stage one analysis, may be referred to as a "threshold value" (sometimes referred to herein as a "reference interference level"). The stage two interference of the best channel is compared to the threshold value, as shown in block 140. If the best channel does not exhibit second stage interference higher than the threshold value, it is selected for communication as shown in block 150. Alternatively, if this best channel exhibits second stage interference above the threshold value, the device disregards this channel and next analyzes the channel with the second lowest level of activity as determined in stage one, and so on until a channel's stage two interference value is not higher than the next best channel's stage one value. This embodiment is useful for efficiently determining the channel with the lowest interference level. After the stage two analysis is complete, the first and second devices may communicate over the selected channel.

The following example is presented for illustrative purposes and is not intended to limit the scope of the claims which follow.

Illustrative Example 1

Stage one searches for interference and the following numbers are returned in millivolts (mV) as the peak interference or signal level observed during the sample time frame. Any unit can be used to represent the relative interference values.

| Stage One Results: | |
| --- | --- |
| Channel | Relative Interference(mV) |
| 1 | 8 |
| 2 | 12 |
| 3 | 14 |
| 4 | 6 |
| 5 | 2 |
| 6 | 7 |
| 7 | 18 |
| 8 | 20 |
| 9 | 4 |
| 10 | 3 |

Based on this example, channel 5 would be selected at the end of stage one because it has the lowest relative interference at 2 mV. Note the next highest amount of interference recorded was channel 10, at 3 mV. Accordingly, in this example, 3 mV is the threshold value.

Based on the results of the first stage, channel 5 would be subjected to second stage analysis. If no instance of interference greater than 3 mV (the next highest level of interference recorded in stage 1) is recorded during stage two analysis of channel 5, the system will select channel 5 for communication.

However, if more than 3 mV of interference is detected in stage two, channel 2 will be rejected and, in this example, channel 10 will be selected for stage two analysis. If the relative interference detected in channel 10 is less than 4 mV (the next highest level of interference detected, in channel 9, during stage one) during stage two, channel 10 will be selected for communication. If more than 4 mV of interference is detected in channel 10 during stage two, channel 9 will be selected for stage two analysis. The system will continue to evaluate each channel in this manner until the interference experienced by a channel during stage two is less than the interference of the next highest interfered with channel as detected in stage one. After a channel has been selected, communication between the first and second devices may take place.

Thus, embodiments of the CHANNEL SELECTION AND MAPPING FOR MEDICAL DEVICE COMMUNICATION are disclosed. One skilled in the art will appreciate that the invention can be practiced with embodiments other than those disclosed. The disclosed embodiments are presented for purposes of illustration and not limitation, and the invention is limited only by the claims that follow.

The invention claimed is:

1. A method of communication between devices comprising:
    initiating a listen before talk (LBT) protocol between first and second devices including implementing a stage one analysis of each of a plurality of frequency channels over a stage one interval to determine a stage one level of interference associated with each channel, at least one of the first and second devices being a medical device and at least one of the first and second devices initiating the LBT protocol;
    choosing one of the channels for a stage two analysis based on the amount of interference associated with each channel; and
    implementing a stage two analysis over a stage two interval to determine a stage two level of interference associated with the one of the channels, the stage two interval being longer than the stage one interval.

2. The method of claim 1, further including determining the channel with the lowest stage one interference level, such channel being the one of the channels analyzed in stage two.

3. The method of claim 2, further including determining the channel with the second lowest stage one interference level defined as a current reference interference level, the stage two analysis including a determination whether the stage two interference level of the one of the channels is lower than the current reference interference level.

4. The method of claim 3, further including selecting the one of the channels over which to conduct communication between the first and second devices if the stage two interference level of the one of the channels is lower than the current reference interference level.

5. The method of claim 3, further including selecting the one of the channels over which to conduct communication between the first and second devices if the stage two interference level of the one of the channels is lower than the stage one interference level of the remainder of the channels.

6. The method of claim 2, further including determining the channels with the first and second next lowest stage one levels of interference relative to the stage one level of interference associated with the channel last analyzed in stage two, the first next lowest stage one level channel being a current tested channel and the second next lowest stage one level channel being a current reference interference level;
    conducting a stage two analysis of the current tested channel to determine a stage two level of interference associated with the current tested channel, the stage two analysis including a determination whether the stage two interference level of the current tested channel is lower than the current reference interference level; and
    selecting the current tested channel over which to conduct communication between the first and second devices if the stage two interference level of the current tested channel is lower than the current reference interference level.

7. The method of claim 6, further comprising repeating the determining and conducting steps until the current tested channel is lower than the current reference interference level.

8. The method of claim 2, further comprising subjecting each channel to stage two analysis until the stage two interference level of one of the channels is less than the stage one interference level of the remaining channels.

9. The method of claim 1, wherein the stage one analysis samples each channel from about 1 msec to about 10 msec and the stage two analysis samples the channel chosen in the stage one analysis from about 10 msec to about 100 msec.

10. The method of claim 1, wherein ten channels are evaluated in the stage one analysis.

11. A medical device comprising:
    a RF antenna;
    a memory that includes instructions defining a listen before talk (LBT) protocol, the LBT protocol including a first stage analysis wherein more than one channel is sampled for interference for a first interval and the channel with the lowest interference is chosen, and a second stage analysis wherein the channel chosen by the first stage analysis is sampled for interference for a second interval, the second interval being longer than the first interval, the channel being selected for RF communication if the second stage interference level is less than the first stage interference level associated with the remainder of the channels; and
    a telemetry circuit functionally coupled to the RF antenna that executes the instructions to perform the LBT protocol.

12. The medical device of claim 11, wherein each channel is evaluated until the interference experienced by a channel during the second stage analysis is less than the interference of a next best channel as detected in the first stage analysis.

13. The medical device of claim 11, wherein the first stage analysis samples each channel from about 1 msec to about 10 msec.

14. The medical device of claim 11, wherein the second stage analysis samples the channel chosen in the first stage analysis from about 10 msec to about 100 msec.

15. The medical device of claim 11, wherein the medical device is an implantable medical device selected from the group consisting of hemodynamic monitors, cardioverter-defibrillators, cardiac pacemakers, cardiac resynchronization therapy pacing devices, drug delivery devices, subcutaneous monitoring devices, subcutaneous therapy devices, and combinations of such devices.

16. A combination of a first device and a second device, comprising:

a first device and a second device each having an RF antenna, at least one of the first device and second device being a medical device; and at least one of the first device and second device having a memory that includes instructions defining a listen before talk (LBT) protocol and a telemetry circuit functionally coupled to its RF antenna that executes the instructions to perform the LBT protocol, the LBT protocol including a first stage analysis wherein more than one channel is sampled for interference for a first interval and the channel with the lowest interference is chosen, and a second stage analysis wherein the channel chosen by the first stage analysis is sampled for interference for a second interval, the second interval being longer than the first interval.

17. The combination of claim 16, wherein each channel is evaluated until the interference experienced by a channel during the second stage analysis is less than the interference of a next best channel as detected in the first stage analysis.

18. The combination of claim 16, wherein the first device is the medical device and the second device is selected from the group consisting of a programmer and a monitor.

19. The combination of claim 18, wherein the first device and second device communicate by RF communication over a distance of about 2 to about 5 meters.

* * * * *